US012558159B2

(12) United States Patent
    Zagorchev

(10) Patent No.: US 12,558,159 B2
(45) Date of Patent: Feb. 24, 2026

(54) LASER INTERSTITIAL THERMAL THERAPY IN THE OPERATING ROOM

(71) Applicant: ClearPoint Neuro, Inc., Solana Beach, CA (US)

(72) Inventor: Lyubomir Zagorchev, Burlington, MA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 371 days.

(21) Appl. No.: 18/350,341

(22) Filed: Jul. 11, 2023

(65) Prior Publication Data

US 2025/0017653 A1      Jan. 16, 2025

(51) Int. Cl.
    *A61B 18/24*      (2006.01)
    *A61B 18/00*      (2006.01)
    *G06T 7/12*       (2017.01)
    *G06V 30/18*      (2022.01)

(52) U.S. Cl.
    CPC .... *A61B 18/24* (2013.01); *A61B 2018/00446* (2013.01); *A61B 2018/00577* (2013.01); *A61B 2018/00803* (2013.01); *G06T 7/12* (2017.01); *G06V 30/1801* (2022.01)

(58) Field of Classification Search
    None
    See application file for complete search history.

(56) References Cited

U.S. PATENT DOCUMENTS

| | | | | |
|---|---|---|---|---|
| 10,751,123 | B2 * | 8/2020 | Leuthardt | .............. A61B 18/22 |
| 2008/0015560 | A1 * | 1/2008 | Gowda | ................. G02B 6/241 |
| | | | | 606/15 |

| | | | | |
|---|---|---|---|---|
| 2016/0297119 | A1 | 10/2016 | Richmond et al. | |
| 2019/0247120 | A1 | 8/2019 | Greenwood et al. | |
| 2020/0372642 | A1 * | 11/2020 | Asemani | ................... G06T 3/02 |
| 2022/0273366 | A1 * | 9/2022 | Varol | ..................... A61B 18/22 |
| 2023/0000561 | A1 | 1/2023 | Zagorchev et al. | |

FOREIGN PATENT DOCUMENTS

| | | |
|---|---|---|
| WO | 2020/069509 A1 | 4/2020 |
| WO | 2023/046960 A1 | 3/2023 |

OTHER PUBLICATIONS

PCT International Search Report and the Written Opinion mailed Oct. 18, 2024, issued in related International Application No. PCT/US2024/037442 (8 pages).

* cited by examiner

*Primary Examiner* — Haris Sabah
(74) *Attorney, Agent, or Firm* — Sheppard Mullin Richter & Hampton LLP

(57)      ABSTRACT

Examples of the presently disclosed technology provide new systems and methods for real-time temperature propagation and tissue damage visualization during laser interstitial thermal therapy (LITT) procedures that do not rely on real-time MR imaging. Accordingly, examples enable performance of LITT procedures in regular operating rooms lacking MR-equipment—thereby reducing costs and improving availability for LITT procedures. Examples achieve these advantages by leveraging "discretized" patient-specific 3D brain structure representations to perform numerical methods for solving partial differential equations that estimate real-time (or close to real-time) temperature propagation within a patient's brain during a LITT procedure.

20 Claims, 7 Drawing Sheets

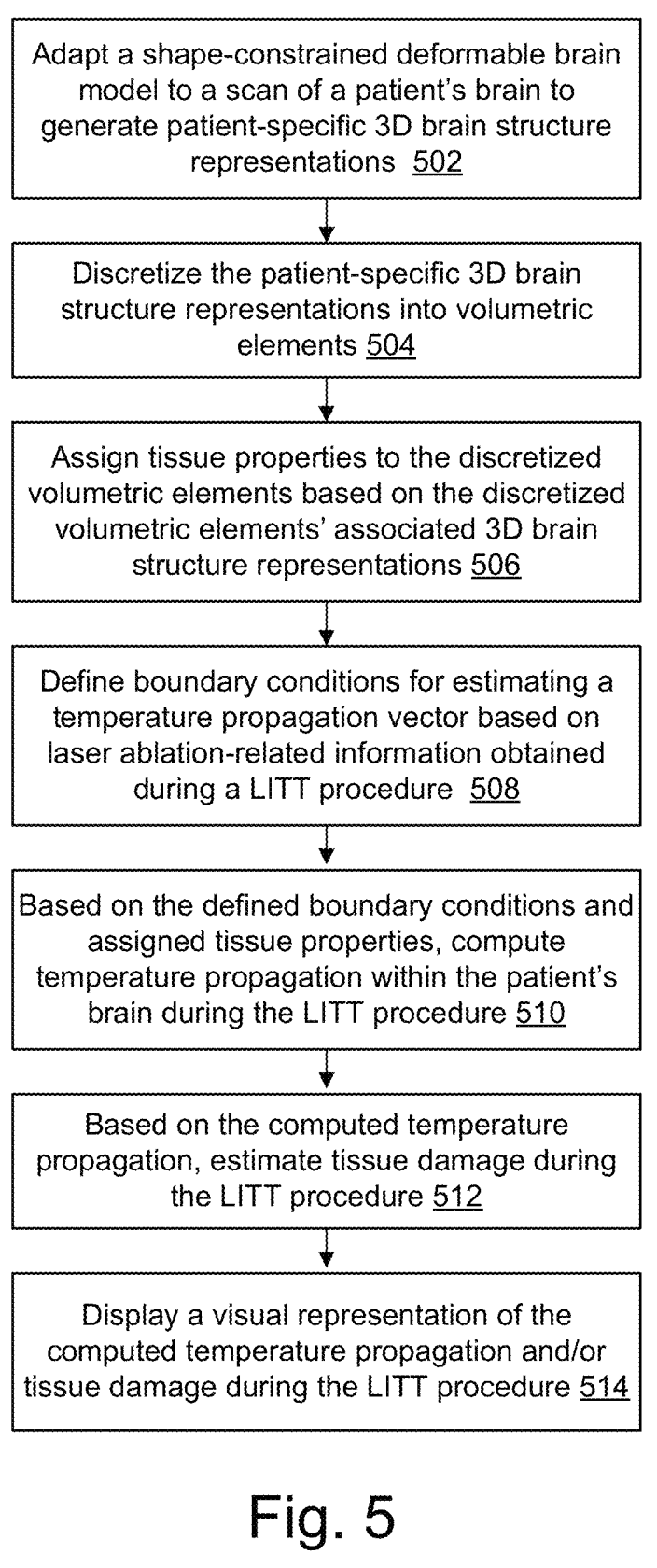

Adapt a shape-constrained deformable brain model to a scan of a patient's brain to generate patient-specific 3D brain structure representations 502

↓

Discretize the patient-specific 3D brain structure representations into volumetric elements 504

↓

Assign tissue properties to the discretized volumetric elements based on the discretized volumetric elements' associated 3D brain structure representations 506

↓

Define boundary conditions for estimating a temperature propagation vector based on laser ablation-related information obtained during a LITT procedure 508

↓

Based on the defined boundary conditions and assigned tissue properties, compute temperature propagation within the patient's brain during the LITT procedure 510

↓

Based on the computed temperature propagation, estimate tissue damage during the LITT procedure 512

↓

Display a visual representation of the computed temperature propagation and/or tissue damage during the LITT procedure 514

Fig. 5

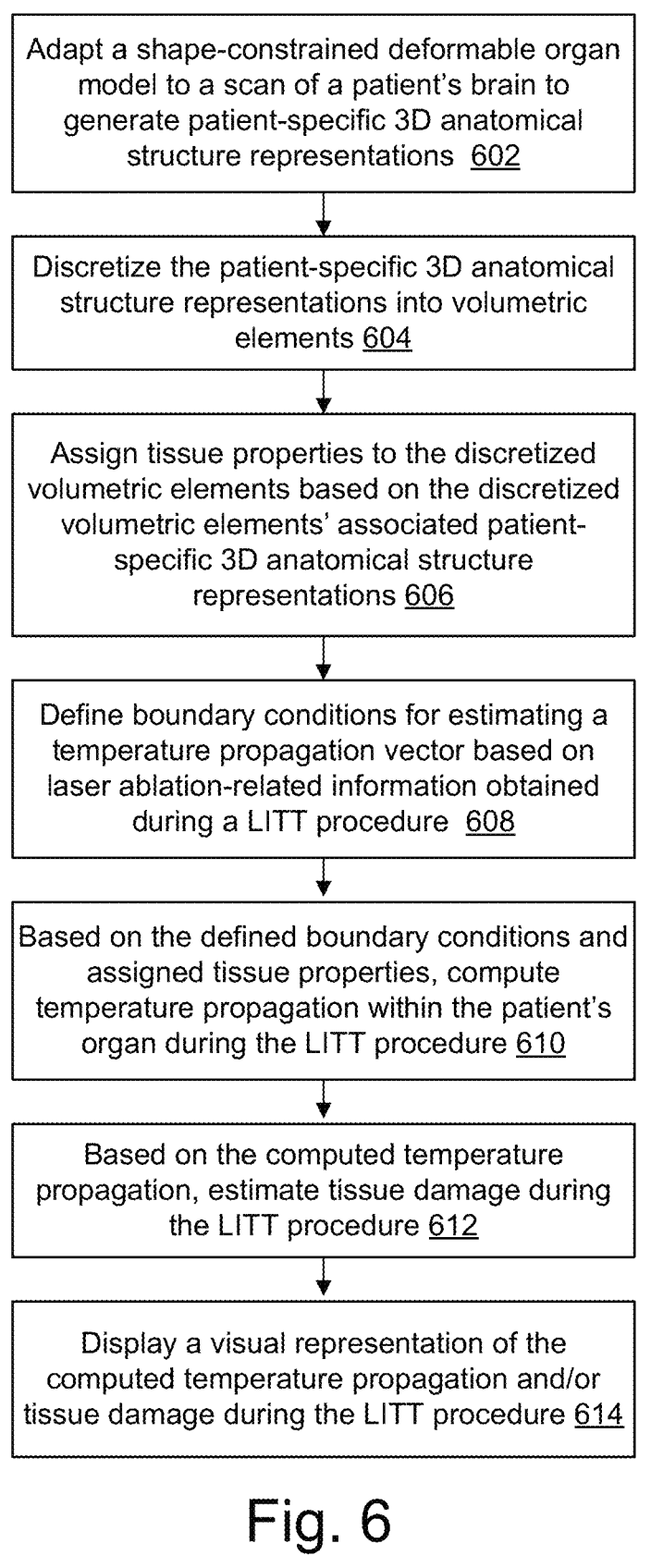

Adapt a shape-constrained deformable organ model to a scan of a patient's brain to generate patient-specific 3D anatomical structure representations  602

Discretize the patient-specific 3D anatomical structure representations into volumetric elements 604

Assign tissue properties to the discretized volumetric elements based on the discretized volumetric elements' associated patient-specific 3D anatomical structure representations 606

Define boundary conditions for estimating a temperature propagation vector based on laser ablation-related information obtained during a LITT procedure  608

Based on the defined boundary conditions and assigned tissue properties, compute temperature propagation within the patient's organ during the LITT procedure 610

Based on the computed temperature propagation, estimate tissue damage during the LITT procedure 612

Display a visual representation of the computed temperature propagation and/or tissue damage during the LITT procedure 614

Fig. 6

LASER INTERSTITIAL THERMAL THERAPY IN THE OPERATING ROOM

TECHNICAL FIELD

The present disclosure relates generally to medical technologies, and more particularly, some examples relate to laser interstitial thermal therapy.

BACKGROUND

Laser interstitial thermal therapy (LITT) is a minimally invasive therapy that ablates (i.e., destroys) problematic tissue of the brain and other organs. For example, LITT has been used to ablate brain tissue that causes seizures.

LITT uses collimated light from a diffusing laser tip to ablate problematic tissues via delivery of thermal energy. For example, heating tissue to temperatures between 40° C. and 60° C. can cause denaturation of DNA and irreversible cell damage. Heating tissue to temperatures above 60° C. can cause instant cell death. Heating tissue to temperatures greater than 100° C. can vaporize water and cause carbonization of surrounding tissue.

BRIEF DESCRIPTION OF THE DRAWINGS

The present disclosure, in accordance with one or more various examples, is described in detail with reference to the following figures. The figures are provided for purposes of illustration only and merely depict examples.

FIG. 5 depicts an example flow diagram for computing and displaying temperature propagation and tissue damage within a patient's brain during a LITT procedure, in accordance with examples of the presently disclosed technology.

FIG. 6 depicts another example flow diagram for computing and displaying temperature propagation and tissue damage within a patient's organ during a LITT procedure, in accordance with examples of the presently disclosed technology.

Figure 1:
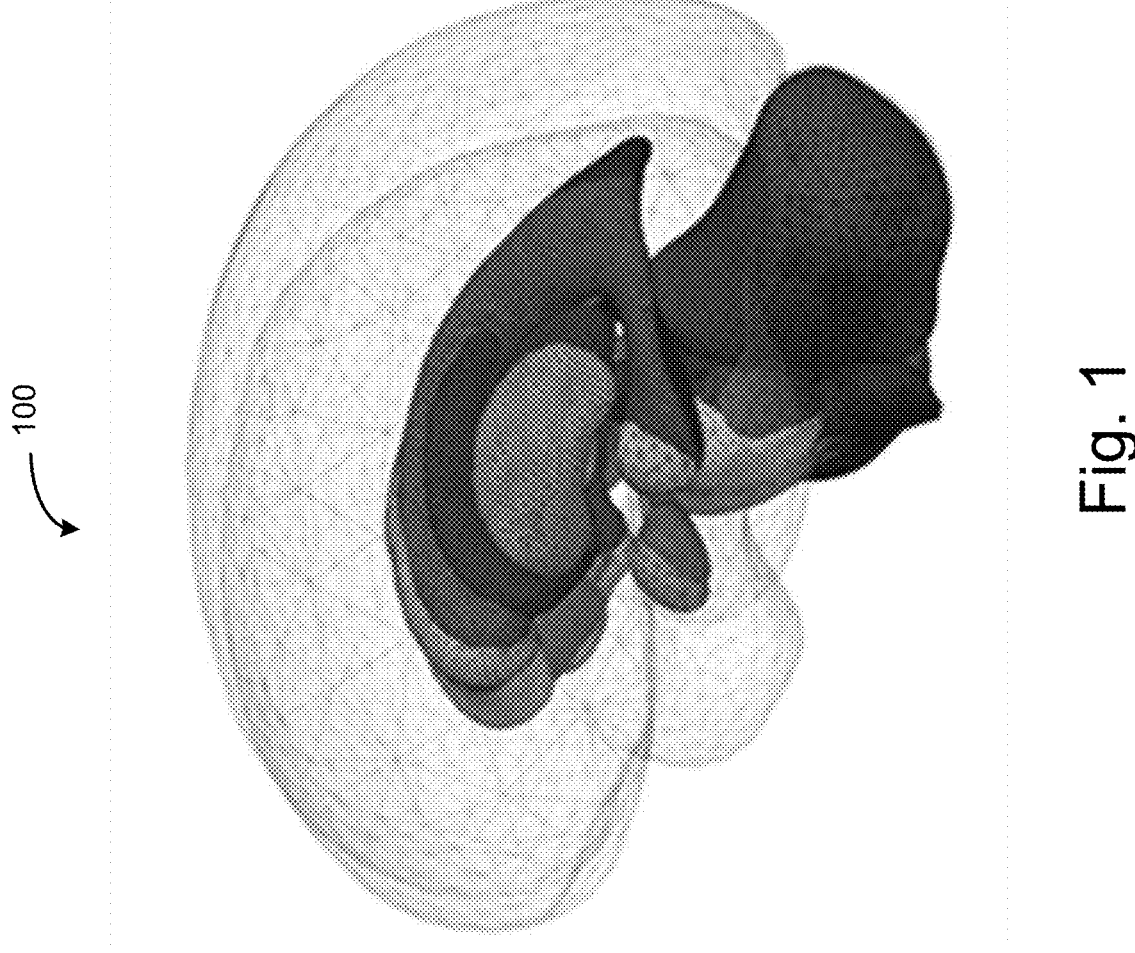
FIG. 1 depicts an example shape-constrained deformable brain model, in accordance with examples of the presently disclosed technology.

The figures are not exhaustive and do not limit the present disclosure to the precise form disclosed.

DETAILED DESCRIPTION

As alluded to above, LITT involves ablating problematic tissues using thermal energy delivered from a laser. Accurate and real-time temperature monitoring of tissues during a LITT procedure can be crucial to ensure that problematic tissue is adequately ablated while minimizing damage to surrounding, non-problematic tissue.

Currently, LITT procedures rely on real-time magnetic resonance (MR) imaging to visualize in-procedure temperature propagation. This may involve using MR-guidance/thermometry to create a real-time (or approximately real-time) thermal image that enables monitoring of laser-tissue interaction and temperature propagation during LITT procedures. Such a real-time thermal image can guide a surgeon during a LITT procedure. For example, based on a real-time thermal image, a surgeon may determine a precise ablation duration that ensures problematic tissue is adequately ablated while minimizing damage to surrounding, non-problematic tissue.

While real-time visualization of temperature propagation can be critical for improving safety and efficacy for LITT procedures, reliance on real-time MR imaging for temperature propagation visualization has certain drawbacks. For example, the MR suites that enable real-time MR imaging can be expensive, and typically have limited availability. As LITT procedures can last multiple hours, they often require booking an MR suite for an entire day. Again, such booking can be expensive and difficult to schedule given the limited availability of many MR suites.

Against this backdrop, examples of the presently disclosed technology provide new systems and methods for real-time temperature propagation and tissue damage visualization during LITT procedures that do not rely on real-time MR imaging. Accordingly, examples enable performance of LITT procedures in regular operating rooms lacking MR-equipment-thereby reducing costs and improving availability for LITT procedures.

Examples achieve these advantages by leveraging "discretized" patient-specific 3D brain structure representations to perform numerical computations for solving partial differential equations (PEDs) that estimate real-time (or close to real-time) temperature propagation within a patient's brain during a LITT procedure. As described in greater detail below, examples can generate the discretized patient-specific 3D brain structure representations by adapting a shape-constrained deformable brain model to a scan of a patient's brain. The shape-constrained deformable brain model may comprise a computerized 3D representation of a non-patient-specific human brain that preserves vertex-based correspondences during adaption to patient scans. Leveraging this unique feature of the shape-constrained deformable brain model (i.e., preservation of vertex-based correspondences during adaption), examples provide reproducible spatial locations for defining boundary conditions across different patients. These boundary conditions can be used in numerical computations for solving PEDs (e.g., the finite element method (FEM), the finite difference method (FDM), the boundary element method (BEM), etc.) that estimate temperature propagation. Defining these boundary conditions in a reproducible, patient-specific manner enables consistent computation and visualization of temperature propagation during LITT procedures across a wide array of patients.

For instance, examples can adapt a shape-constrained deformable brain model to a scan (e.g., an MR scan, a CT scan, a PET scan, etc.) of a patient's brain to generate patient-specific 3D brain structure representations representing different structures of the patient's brain (e.g., the cerebral cortex, sub-cortical structures, etc.). The scan may be obtained prior to, or during, a LITT procedure. As alluded to above, the shape-constrained deformable brain model may comprise a computerized 3D representation of a non-patient-specific brain that preserves vertex-based correspondences during adaption to patient scans.

Upon generating the patient-specific 3D brain structure representations, examples can discretize the patient-specific 3D brain structure representations into volumetric elements (e.g., tetrahedrons, hexahedrons, etc.). As alluded to above, and as described in greater detail below, examples can leverage these discrete volumetric elements to perform numerical computations for solving PEDs that estimate temperature propagation in the patient's brain.

Examples can assign tissue properties (e.g., thermal conductivity coefficients, perfusion coefficients, etc.) to the discretized volumetric elements based on the discretized volumetric mesh elements' associated patient-specific 3D brain structure representations. Different brain structures often comprise different tissue types, and accordingly have different tissue properties. For example, a first brain structure may comprise white matter (e.g., a first tissue type), a second brain structure may comprise grey matter (e.g., second tissue type), and a third brain structure may comprise cerebrospinal fluid (e.g., a third tissue type). Relatedly, certain subcortical regions may comprise both white and grey matter. Temperature may propagate differently in brain structures based on their respective tissue types and associated tissue properties. Relatedly, tissue damage may evolve differently (e.g., in response to temperature propagation) in different brain structures based on their respective tissue types and associated tissue properties. As alluded to above (and as described in greater detail below), examples account for these tissue property differences by segmenting a shape-constrained deformable brain model to generate patient-specific 3D brain structure representations (i.e., segments) representing different anatomical regions of the patient's brain. Accordingly, constituent discrete volumetric elements of a first patient-specific 3D brain structure representation may be assigned a first set of tissue properties (e.g., a set of tissue properties for white matter), constituent discrete volumetric elements of a second patient-specific 3D brain structure representation may be assigned a second set of tissue properties (e.g., a set of tissue properties for grey matter), and constituent discrete volumetric elements of a third patient-specific 3D brain structure representation may be assigned a third set of tissue properties (e.g., a set of tissue properties for cerebrospinal fluid).

Upon assigning tissue properties (e.g., thermal conductivity coefficients, perfusion coefficients, etc.) to the discrete volumetric mesh elements, examples can define boundary conditions for estimating a temperature propagation vector based on laser ablation-related information obtained during the LITT procedure. As alluded to above, numerical computations (e.g., FEM, FDM, BEM, etc.) for solving PEDs often involve dividing a space into finite elements. Solving PEDs via these numerical computations also requires defining boundary conditions. For example, boundary conditions may be related to laser ablation-related parameters that estimate a temperature propagation vector during the LITT procedure (e.g., location of a diffusion tip of a laser inserted into the patient's brain during the LITT procedure, an estimated direction vector for a light beam emitted from the diffusion tip of the laser, and real-time operational settings of the laser such as wavelength of emitted light, power output of the laser, etc.). Boundary conditions can also be defined for discretized volumetric elements on the boundary of the patient-specific 3D brain structure representations.

Based on the defined boundary conditions and assigned tissue properties, examples can compute temperature propagation within the patient's brain during the LITT procedure via a numerical computation for solving a PED (e.g., FEM, FDM, BEM, etc.). Examples can then display a visual representation of the computed temperature propagation (e.g., color-coded heat map that dynamically changes color based on the computed temperature propagation). In various cases, examples can also estimate tissue damage within the patient's brain during the LITT procedure based on the computed temperature propagation—and display a visual representation of the estimated tissue damage (e.g., a second color-coded heat map that dynamically changes color based on the estimated tissue damage).

In various implementations, the above-described temperature propagation computation may involve multiple (e.g., several hundred) time-steps over the course of the LITT procedure. This iterative computation may be non-linear as tissue properties generally change with temperature. Thus, examples may, at each time-step: (1) assign new tissue properties to the discrete volumetric mesh elements; and (2) compute new temperatures associated with the discrete volumetric elements based on the newly updated tissue properties.

The principles disclosed herein may be applied in contexts other than LITT procedures in the brain. For example, the same/similar principles may be applied for LITT procedures in other organs (e.g., liver, heart, etc.) comprised of different anatomical structures and associated different tissue properties.

As alluded to above, examples of the present technology provide numerous advantages. For instance, by providing new systems and methods for real-time visualization of temperature propagation and tissue damage during LITT procedures that do not rely on real-time MR imaging, examples enable performance of LITT procedures in regular operating rooms lacking MR-equipment-thereby reducing costs and improving availability for LITT procedures. Relatedly, by accurately computing/displaying temperature propagation and/or tissue damage for LITT procedures in real-time, examples can improve safety and efficacy for LITT procedures-thereby improving patient outcomes and reducing costs.

Examples of the presently disclosed technology will be described in greater detail in conjunction with the following FIGs.

FIG. 1 depicts an example shape-constrained deformable brain model 100, in accordance with examples of the presently disclosed technology. Shape-constrained deformable brain model 100 may be a computerized 3D representation of a generalized human brain (i.e., a non-patient-specific 3D representation of the human brain) that preserves vertex-based correspondences during adaption to patient-specific data/scans using shape-constrained deformation. Shape-constrained deformable brain model 100 can be derived as an average/mean representation from a set of training data.

As depicted, in certain examples shape-constrained deformable brain model 100 may comprise mesh elements and mesh vertices at the junctions of adjoining/adjacent mesh elements. Each mesh element of shape-constrained deformable brain model 100 may represent a different brain region. In the specific example of FIG. 1, the mesh elements of shape-constrained deformable brain model 100 comprise triangles, but in other examples mesh elements may comprise different shapes.

In general, a mesh may refer to a representation of a larger domain (e.g., a volume or surface) comprised of smaller discrete cells called mesh elements, and mesh vertices at the junctions of adjacent/adjoining mesh elements. Meshes can be used to compute solutions to equations across individual mesh elements, which then can be used to approximate solutions over the larger domain. As examples of the present technology are designed in appreciation of, mesh elements (or discretized volumetric mesh elements derived from mesh elements) can be used to perform numerical computations for solving PEDs that estimate temperature propagation within a patient's brain.

While in the specific example of FIG. 1 shape-constrained deformable brain model 100 comprises a 3D mesh, in other examples shape-constrained deformable brain model 100 may comprise other types of representations that can define geometry of anatomical brain regions (e.g., a parametric surface, a point cloud, etc.).

As depicted (and as will be discussed below), shape-constrained deformable brain model 100 may comprise individual 3D segments/sub-representations representing various structures of the brain (e.g., the cerebral cortex, sub-cortical structures, cerebral spinal fluid, etc.).

Figure 2:
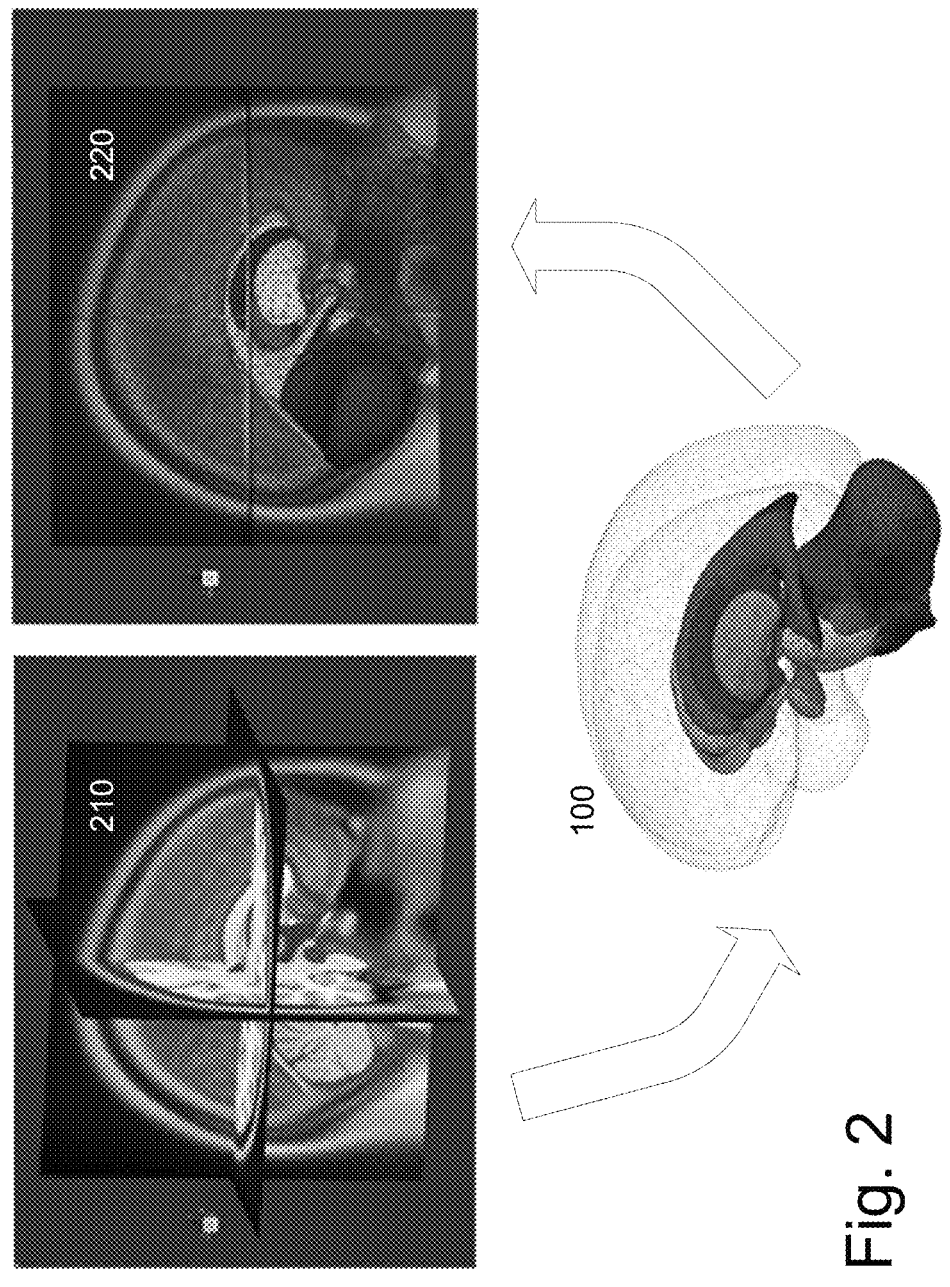
FIG. 2 depicts an example adaption of a shape-constrained deformable brain model to a scan of a patient's brain to generate a patient-specific 3D brain representation, in accordance with examples of the presently disclosed technology.

FIG. 2 depicts an example adaption of shape-constrained deformable brain model 100 to a scan 210 of a patient's brain to generate a patient-specific 3D brain representation 220, in accordance with examples of the presently disclosed technology.

As alluded to above, shape-constrained deformable brain model 100 can be adapted to a scan of a patient's brain to generate a patient-specific 3D brain representation. As depicted in FIG. 2, a patient-specific 3D brain representation may comprise individual 3D sub-representations/segments representing individual brain structures of the patient (i.e., patient-specific 3D brain structure representations). Importantly (and as alluded to above), examples can achieve this adaptation with just a single scan of the patient's brain. Accordingly, examples do not require booking an MR suite for the entirety of a LITT procedure. Instead, examples simply require a single scan of a patient's brain (this scan can be an MR scan, but also other types of scans such as CT or PET scans) that may be obtained prior to a LITT procedure. Accordingly, examples can enable performance of LITT procedures in regular operating rooms lacking MR-equipment—thereby reducing costs and improving availability for LITT procedures.

As described above, shape-constrained deformable brain model 100 may be a computerized 3D representation of a generalized human brain (i.e., a non-patient-specific 3D representation of the human brain) that preserves vertex-based correspondences during adaption to patient-specific data/scans using shape-constrained deformation. Shape-constrained deformation may constrain deformation to an apriori derived mean shape (i.e., shape-constrained deformable brain model 100). The shape-constrained deformation can use a penalty term estimated from the mean shape (i.e., estimated from shape-constrained deformable brain model 100) that prevents topological changes during adaptation, which may be an iterative process. Segmentation (i.e., generation of individual/segmented patient-specific 3D brain structure representations) may gradually deform the mean shape (i.e., gradually deform shape-constrained deformable brain model 100) to match the patient-specific scan/image. In other words, shape may be constrained to the mean shape (i.e., constrained to shape-constrained deformable brain model 100), which can grow or shrink without morphing into a different shape.

Through the above-described adaptation, vertex-based correspondences can be preserved between vertices of shape-constrained deformable brain model 100 and vertices of the patient-specific 3D brain structure representations generated from shape-constrained deformable brain model 100. As alluded to above, leveraging this unique feature of shape-constrained deformable brain model 100 (i.e., preservation of vertex-based correspondences during adaption), examples provide reproducible spatial locations for defining boundary conditions for numerical computations for solving PEDs across different patients. Defining these boundary conditions in a reproducible, patient-specific manner enables consistent computation and visualization of temperature propagation and tissue damage during LITT procedures across many patients.

Figure 3:
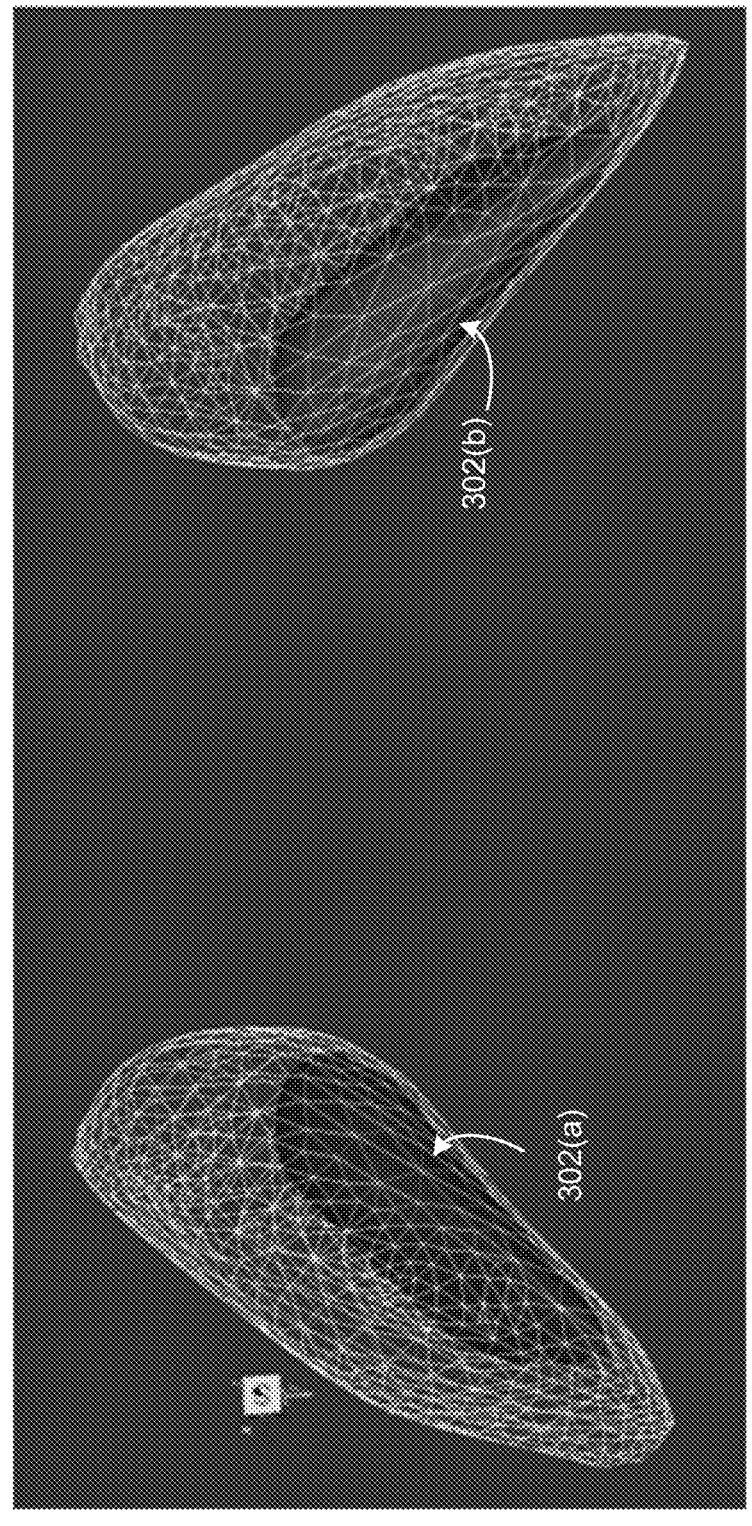
FIG. 3 depicts two example patient-specific 3D brain structure representations, in accordance with examples of the presently disclosed technology.

FIG. 3 depicts example patient-specific 3D brain structure representations 302(a) and 302(b), in accordance with examples of the presently disclosed technology. Here patient-specific 3D brain structure representations 302(a) and 302(b) may be individual segments/sub-representations of patient-specific 3D brain representation 220 and may represent the patient's right and left internal globus pallidus (GPi) lobes respectively.

Figure 4:
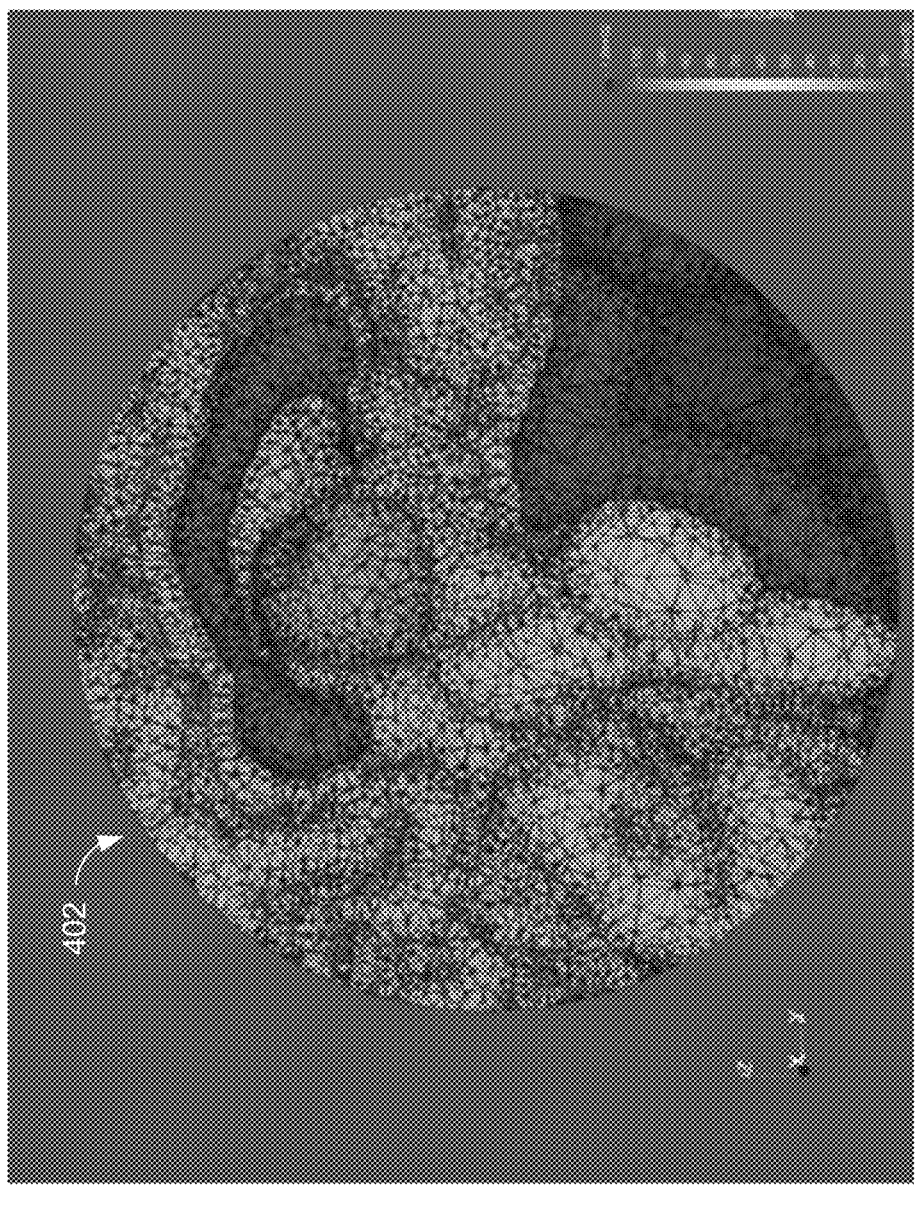
FIG. 4 depicts an example discretized patient-specific 3D brain structure representation, in accordance with examples of the presently disclosed technology.

FIG. 4 depicts an example discretized patient-specific 3D brain structure representation 402, in accordance with examples of the presently disclosed technology. As alluded to above, examples can discretize a patient-specific 3D brain structure representation into "discretized" volumetric elements. Examples can use various techniques to perform such discretization. For instance, examples can utilize a meshing library, such as CGAL.

As depicted in FIG. 4, in certain implementations examples can utilize a sphere to limit the solution for faster computations. Accordingly, the patient-specific 3D brain structure representation can be discretized within the sphere.

It should be understood that the principles described in conjunction with FIGS. 1-4 may be applied to other organs (e.g., liver, heart, etc.) comprised of different anatomical structures and associated different tissue properties. For example, shape-constrained deformable brain model 100 may instead be replaced by a shape-constrained deformable organ model that is a computerized 3D representation of a generalized organ (i.e., a non-patient-specific 3D representation of an organ) that preserves vertex-based correspondences during adaption to patient-specific data/scans. Relatedly, patient-specific 3D brain representation 220 may instead be a patient-specific 3D organ representation 220 that represents an organ of a patient (e.g., the liver or heart of the patient). Similarly, patient-specific 3D brain structure representations 302(a) and 302(b) may instead be individual segments/sub-representations of a patient-specific 3D organ representation and may represent different anatomical structures of the organ (e.g., ventricles and/or atriums of a heart, lobes and ligaments of a liver, etc.).

FIG. 5 depicts an example flow diagram for computing and displaying temperature propagation and tissue damage within a patient's brain during a LITT procedure, in accordance with examples of the presently disclosed technology.

At operation 502, examples adapt a shape-constrained deformable brain model to a scan (e.g., an MR scan, a CT scan, a PET scan, etc.) of a patient's brain to generate patient-specific 3D brain structure representations. The scan may be obtained prior to, or during, a LITT procedure. As alluded to above, the shape-constrained deformable brain model may comprise a computerized 3D representation of a non-patient-specific human brain that preserves vertex-based correspondences during adaption to patient scans.

At operation 504, examples discretize the patient-specific 3D brain structure representations into volumetric elements (e.g., tetrahedrons, hexahedrons, etc.). As alluded to above, examples can leverage these discrete volumetric elements in numerical computations (e.g., FEM, FDM, BEM, etc.) for solving PEDs that estimate temperature propagation in the patient's brain.

At operation 506, examples assign tissue properties (e.g., thermal conductivity coefficients, perfusion coefficients, etc.) to the discretized volumetric elements based on the discretized volumetric elements' associated patient-specific 3D brain structure representations. Different brain structures often comprise different tissue types, and accordingly have different tissue properties. For example, a first brain structure may comprise white matter (e.g., a first tissue type), a second brain structure may comprise grey matter (e.g., second tissue type), and a third brain structure may comprise cerebrospinal fluid (e.g., a third tissue type). Temperature may propagate differently in each of the three brain structures based on their respective tissue types and associated tissue properties. As alluded to above, examples account for these differences by applying the shape-constrained deformable brain model to the patient's scan to generate the patient-specific 3D brain structure representations (i.e., segments) representing different brain structures/regions of the patient's brain. Accordingly, constituent discrete volumetric elements of a first patient-specific 3D brain structure representation may be assigned a first set of tissue properties (e.g., a set of tissue properties for white matter), constituent discrete volumetric elements of a second patient-specific 3D brain structure representation may be assigned a second set of tissue properties (e.g., a set of tissue properties for grey matter), and constituent discrete volumetric elements of a third patient-specific 3D brain structure representation may be assigned a third set of tissue properties (e.g., a set of tissue properties for cerebrospinal fluid).

At operation 508, examples define boundary conditions for estimating a temperature propagation vector based on laser ablation-related information obtained during the LITT procedure. As alluded to above, numerical computations (e.g., FEM, FDM, BEM, etc.) for solving PEDS often involve dividing a space into finite elements. Solving PEDs via these numerical computations also requires defining boundary conditions. For example, boundary conditions may be related to laser ablation-related parameters that estimate a temperature propagation vector during the LITT procedure (e.g., location of a diffusion tip of a laser inserted into the patient's brain during the LITT procedure, an estimated direction vector for a light beam emitted from the diffusion tip of the laser, and real-time operational settings of the laser such as wavelength of emitted light, power output of the laser, etc.). Boundary conditions can also be defined for discretized volumetric elements on the boundary of the patient-specific 3D brain structure representations.

At operation 510, based on the defined boundary conditions and the assigned tissue properties, examples compute temperature propagation within the patient's brain during the LITT procedure. As alluded to above, this may involve performing a numerical computation (e.g., FEM, FDM, BEM) using the defined boundary conditions and the tissue properties assigned to the discretized volumetric elements of the patient-specific 3D brain structure representations.

At operation 512, examples estimate tissue damage within the patient's brain during the LITT procedure based on the computed temperature propagation. This may comprise leveraging models that correlate tissue temperature with tissue damage.

At operation 514, examples display at least one of a visual representation of the computed temperature propagation and a visual representation of the estimated tissue damage. The visual representation of the computed temperature propagation may comprise a color-coded heat map that dynamically changes color based on the computed temperature propagation. The visual representation of the estimated tissue damage may comprise a second color-coded heat map that dynamically changes color based on the estimated tissue damage.

In various implementations, operations 506-514 may be performed iteratively over multiple (e.g., several hundred) time-steps over the course of the LITT procedure. This iterative computation may be non-linear as tissue properties generally change with temperature. Thus, examples may, at each time-step: (1) assign new tissue properties to the discrete volumetric elements (i.e., an iteration of operation 506); and (2) compute new temperatures associated with the discrete volumetric elements based on the newly updated tissue properties. Here, the patient-specific reproducibility of the present technology can make these iterative computations more consistent across different subjects.

As alluded to above, the same/similar principles described in conjunction with FIG. 5 may be applied for LITT procedures in other organs (e.g., liver, heart, etc.) comprised of different anatomical structures and associated different tissue properties.

Accordingly, FIG. 6 depicts an example flow diagram for computing and displaying temperature propagation and tissue damage within a patient's organ during a LITT procedure, in accordance with examples of the presently disclosed technology.

At operation 602, examples adapt a shape-constrained deformable organ model to a scan (e.g., an MR scan, a CT scan, a PET scan, etc.) of a patient's organ to generate patient-specific 3D anatomical structure representations representing anatomical structures of the patient's organ. The scan may be obtained prior to, or during, a LITT procedure. As alluded to above, the shape-constrained deformable organ model may comprise a computerized 3D representation of a non-patient-specific organ that preserves vertex-based correspondences during adaption to patient scans.

At operation 604, examples discretize the patient-specific 3D anatomical structure representations into volumetric elements (e.g., tetrahedrons, hexahedrons, etc.). As alluded to above, examples can leverage these discrete volumetric elements in numerical computations (e.g., FEM, FDM, BEM, etc.) for solving PEDs that estimate temperature propagation in the patient's organ.

At operation 606, examples assign tissue properties (e.g., thermal conductivity coefficients, perfusion coefficients, etc.) to the discretized volumetric elements based on the discretized volumetric elements' associated patient-specific 3D anatomical structure representations. Just as different brain structures can comprise different tissue types, and accordingly have different tissue properties, anatomical structures of other organs can also comprise different tissue types, and accordingly have different tissue properties. As alluded to above, examples account for these differences by applying the shape-constrained deformable organ model to generate the patient-specific 3D anatomical structure representations (i.e., segments) of the patient's organ. Accordingly, constituent discrete volumetric elements of a first patient-specific 3D anatomical structure representation representing a first anatomical structure of the patient's organ may be assigned a first set of tissue properties, constituent discrete volumetric elements of a second patient-specific 3D anatomical structure representation representing a second anatomical structure of the patient's organ may be assigned a second set of tissue properties, and so on.

At operation 608, examples define boundary conditions for estimating a temperature propagation vector based on laser ablation-related information obtained during the LITT procedure. As alluded to above, numerical computations (e.g., FEM, FDM, BEM, etc.) for solving PEDs often involve dividing a space into finite elements. Solving PEDs via these numerical computations also requires defining boundary conditions. For example, boundary conditions may be related to laser ablation-related parameters that estimate a temperature propagation vector during the LITT procedure (e.g., location of a diffusion tip of a laser inserted into the patient's organ during the LITT procedure, an estimated direction vector for a light beam emitted from the diffusion tip of the laser, and real-time operational settings of the laser such as wavelength of emitted light, power output of the laser, etc.). Boundary conditions can also be defined for discretized volumetric elements on the boundary of the patient-specific 3D anatomical structure representations.

At operation 610, based on the defined boundary conditions and the assigned tissue properties, examples compute temperature propagation within the patient's organ during the LITT procedure. As alluded to above, this may involve performing a numerical computation (e.g., FEM, FDM, BEM) using the defined boundary conditions and the tissue properties assigned to the discretized volumetric elements of the patient-specific 3D anatomical structure representations.

At operation 612, examples estimate tissue damage within the patient's organ during the LITT procedure based on the computed temperature propagation. This may comprise leveraging models that correlate tissue temperature with tissue damage.

At operation 614, examples display at least one of a visual representation of the computed temperature propagation and a visual representation of the estimated tissue damage. The visual representation of the computed temperature propagation may comprise a color-coded heat map that dynamically changes color based on the computed temperature propagation. The visual representation of the estimated tissue damage may comprise a second color-coded heat map that dynamically changes color based on the estimated tissue damage.

In various implementations, operations 606-614 may be performed iteratively over multiple (e.g., several hundred) time-steps over the course of the LITT procedure. This iterative computation may be non-linear as tissue properties generally change with temperature. Thus, examples may, at each time-step: (1) assign new tissue properties to the discrete volumetric elements (i.e., an iteration of operation 606); and (2) compute new temperatures associated with the discrete volumetric elements based on the newly updated tissue properties. Here, the patient-specific reproducibility of the present technology can make these iterative computations more consistent across different subjects.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAS, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and

Figure 7:
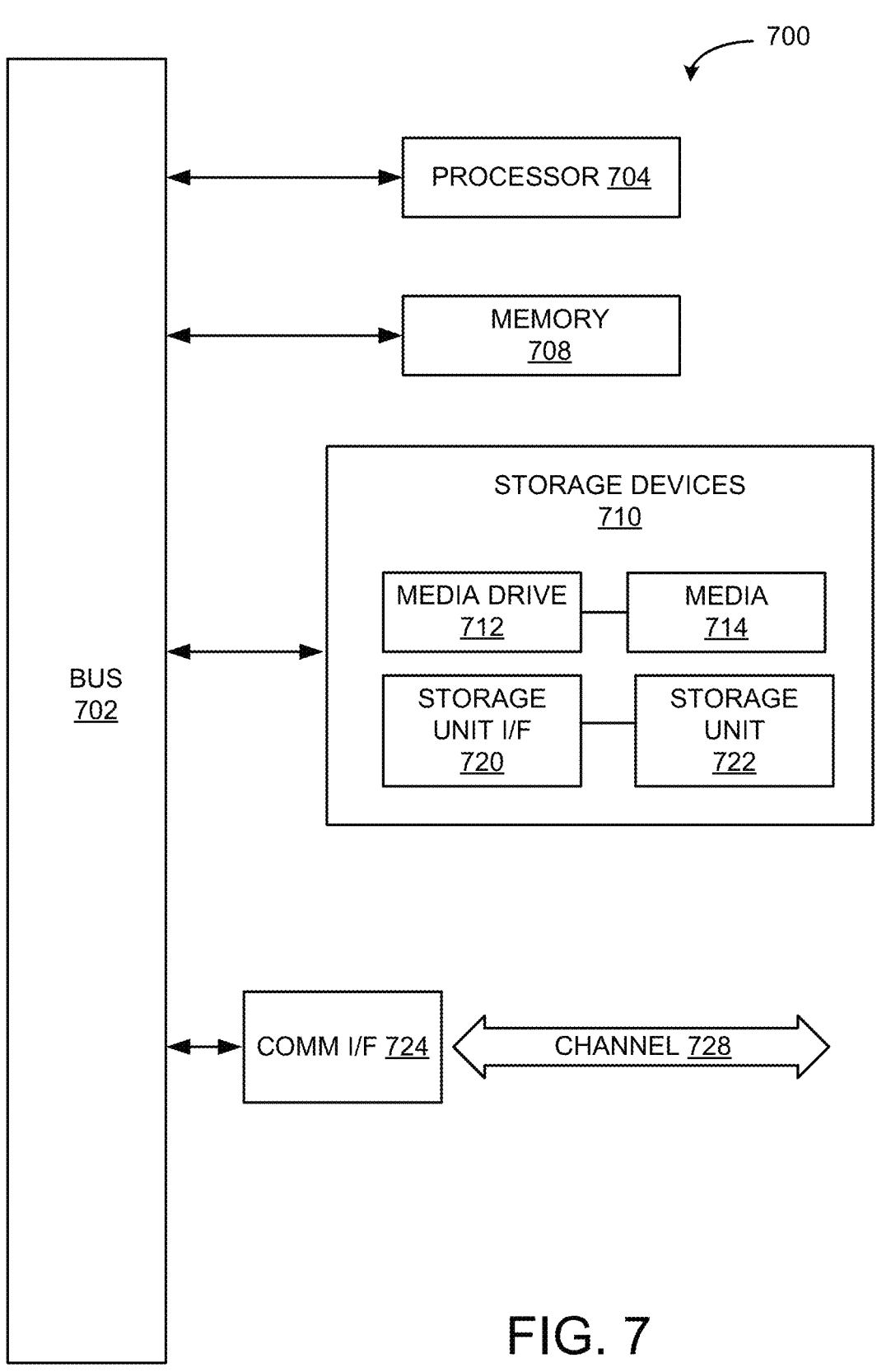
FIG. 7 is an example computing component that may be used to implement various features of examples described in the present disclosure.

10 permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 7. Various examples are described in terms of this example-computing component 700. After reading this description, it will become apparent to a person skilled in the relevant art how to implement the application using other computing components or architectures.

Referring now to FIG. 7, computing component 700 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 700 might also represent computing capabilities embedded within or otherwise available to a given device. For example, a computing component might be found in other electronic devices such as, for example, portable computing devices, and other electronic devices that might include some form of processing capability.

Computing component 700 might include, for example, one or more processors, controllers, control components, or other processing devices. Processor 704 might be implemented using a general-purpose or special-purpose processing engine such as, for example, a microprocessor, controller, or other control logic. Processor 704 may be connected to a bus 702. However, any communication medium can be used to facilitate interaction with other components of computing component 700 or to communicate externally.

Computing component 700 might also include one or more memory components, simply referred to herein as main memory 708. For example, random access memory (RAM) or other dynamic memory, might be used for storing information and instructions to be executed by processor 704. Main memory 708 might also be used for storing temporary variables or other intermediate information during execution of instructions to be executed by processor 704. Computing component 700 might likewise include a read only memory ("ROM") or other static storage device coupled to bus 702 for storing static information and instructions for processor 704.

The computing component 700 might also include one or more various forms of information storage mechanism 710, which might include, for example, a media drive 712 and a storage unit interface 720. The media drive 712 might include a drive or other mechanism to support fixed or removable storage media 714. For example, a hard disk drive, a solid-state drive, a magnetic tape drive, an optical drive, a compact disc (CD) or digital video disc (DVD) drive (R or RW), or other removable or fixed media drive might be provided. Storage media 714 might include, for example, a hard disk, an integrated circuit assembly, magnetic tape, cartridge, optical disk, a CD or DVD. Storage media 714 may be any other fixed or removable medium that is read by, written to or accessed by media drive 712. As these examples illustrate, the storage media 714 can include a computer usable storage medium having stored therein computer software or data.

In alternative examples, information storage mechanism 710 might include other similar instrumentalities for allowing computer programs or other instructions or data to be loaded into computing component 700. Such instrumentalities might include, for example, a fixed or removable storage unit 722 and an interface 720. Examples of such storage units 722 and interfaces 720 can include a program cartridge and cartridge interface, a removable memory (for example, a flash memory or other removable memory component) and memory slot. Other examples may include a PCMCIA slot and card, and other fixed or removable storage units 722 and interfaces 720 that allow software and data to be transferred from storage unit 722 to computing component 700.

Computing component 700 might also include a communications interface 724. Communications interface 724 might be used to allow software and data to be transferred between computing component 700 and external devices. Examples of communications interface 724 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 724 may be carried on signals, which can be electronic, electromagnetic (which includes optical) or other signals capable of being exchanged by a given communications interface 724. These signals might be provided to communications interface 724 via a channel 728. Channel 728 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 708, storage unit 720, media 714, and channel 728. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 700 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

The invention claimed is:

1. A non-magnetic resonance (MR)-guided method for visualizing temperature propagation during a laser interstitial thermal therapy (LITT) procedure, comprising:

adapting a shape-constrained deformable brain model to a scan of a patient's brain to generate patient-specific 3D brain structure representations;

discretizing the patient-specific 3D brain structure representations into volumetric elements;

assigning tissue properties to the discretized volumetric elements based on the discretized volumetric elements' associated patient-specific 3D brain structure representations;

defining boundary conditions for estimating a temperature propagation vector based on laser ablation-related information obtained during the LITT procedure;

based on the defined boundary conditions and the assigned tissue properties, computing temperature propagation within the patient's brain during the LITT procedure; and displaying a visual representation of the computed temperature propagation during the LITT procedure.

2. The non-MR guided method of claim 1, wherein computing the temperature propagation within the patient's brain during the LITT procedure comprises:

iteratively computing temperatures associated with the discretized volumetric elements over multiple time steps.

3. The non-MR guided method of claim 2, wherein assigning tissue properties to the discretized volumetric elements based on the discretized volumetric elements' associated brain structures comprises:

iteratively, for the multiple time steps, assigning tissue properties to the discretized volumetric elements based on the discretized volumetric elements' associated patient-specific 3D brain structure representations and the iteratively computed temperatures associated with the discretized volumetric elements.

4. The non-MR guided method of claim 1, wherein the shape-constrained deformable brain model comprises a computerized 3D representation of a non-patient-specific human brain that preserves vertex-based correspondence during adaption to patient scans.

5. The non-MR guided method of claim 1, further comprising:

estimating tissue damage within the patient's brain during the LITT procedure based on the computed temperature propagation; and displaying a visual representation of the estimated tissue damage within the patient's brain during the LITT procedure.

6. The non-MR guided method of claim 1, wherein the laser ablation-related information comprises at least one of:

location of a diffusion tip of a laser within the patient's brain;

an estimated direction vector for a laser beam emitted from the diffusion tip; and settings of the laser during the LITT procedure.

7. The non-MR guided method of claim 1, wherein the visual representation of the computed temperature propagation within the patient's brain during the LITT procedure comprises a color-coded heat map that dynamically changes color based on the computed temperature propagation.

8. The non-MR guided method of claim 1, wherein assigning the tissue properties to the discretized volumetric elements based on the discretized volumetric elements' associated patient-specific 3D brain structure representations comprises:

assigning, to discretized volumetric elements of a first patient-specific 3D brain structure representation of the patient-specific 3D brain structure representations, a first set of tissue properties; and assigning, to discretized volumetric elements of a second patient-specific 3D brain structure representation of the patient-specific 3D brain structure representations, a second set of tissue properties.

9. The non-MR guided method of claim 1, wherein the tissue properties comprise at least one of thermal conductivity coefficients and perfusion coefficients.

10. A non-transitory computer-readable storage medium including instructions that, when executed by at least one processor of a computing system, cause the computing system to perform a method comprising:

adapting a shape-constrained deformable organ model to a scan of a patient's organ to generate patient-specific 3D anatomical structure representations representing anatomical structures of the patient's organ;

discretizing the patient-specific 3D anatomical structure representations into volumetric elements;

assigning tissue properties to the discretized volumetric elements based on the discretized volumetric elements' associated patient-specific 3D anatomical structure representations;

defining boundary conditions for estimating a temperature propagation vector based on laser ablation-related information obtained during a laser interstitial thermal therapy (LITT) procedure;

based on the defined boundary conditions and the assigned tissue properties, computing temperature propagation within the patient's organ during the LITT procedure; and displaying a visual representation of the computed temperature propagation during the LITT procedure.

11. The non-transitory computer-readable storage medium of claim 10, wherein computing the temperature propagation within the patient's organ during the LITT procedure comprises:

iteratively computing temperatures associated with the discretized volumetric elements over multiple time steps.

12. The non-transitory computer-readable storage medium of claim 11, wherein assigning tissue properties to the discretized volumetric elements based on the discretized volumetric elements' associated patient-specific 3D anatomical structure representations comprises:

iteratively, for the multiple time steps, assigning tissue properties to the discretized volumetric elements based on the discretized volumetric elements' associated patient-specific 3D anatomical structure representations and the iteratively computed temperatures associated with the discretized volumetric elements.

13. The non-transitory computer-readable storage medium of claim 10, wherein the shape-constrained deformable organ model comprises a computerized 3D representation of a non-patient-specific organ corresponding with the patient's organ that preserves vertex-based correspondences during adaption to patient scans.

14. The non-transitory computer-readable storage medium of claim 10, wherein the method further comprises:

estimating tissue damage within the patient's organ during the LITT procedure based on the computed temperature propagation; and displaying a visual representation of the estimated tissue damage within the patient's organ during the LITT procedure.

15. The non-transitory computer-readable storage medium of claim 10, wherein the laser ablation-related information comprises:

location of a diffusion tip of a laser within the patient's organ;

an estimated direction vector for a laser beam emitted from the diffusion tip; and settings of the laser during the LITT procedure.

16. The non-transitory computer-readable storage medium of claim 10, wherein the visual representation of the computed temperature propagation within the patient's organ during the LITT procedure comprises a color-coded heat map that dynamically changes color based on the computed temperature propagation.

17. The non-transitory computer-readable storage medium of claim 10, wherein assigning the tissue properties to the discretized volumetric elements based on the discretized volumetric elements' associated patient-specific 3D anatomical structure representations comprises:

assigning, to discretized volumetric elements of a first patient-specific 3D anatomical structure representation of the patient-specific 3D anatomical structure representations, a first set of tissue properties; and assigning, to discretized volumetric elements of a second patient-specific 3D anatomical structure representation of the patient-specific 3D anatomical structure representations, a second set of tissue properties.

18. The non-transitory computer-readable storage medium of claim 10, wherein the tissue properties comprise at least one of thermal conductivity coefficients and perfusion coefficients.

19. A system comprising:

at least one processor; and a memory storing instructions that, when executed by the at least one processor, cause the system to perform a method comprising:

adapting a shape-constrained deformable brain model to a scan of a patient's brain to generate patient-specific 3D brain structure representations;

discretizing the patient-specific 3D brain structure representations into volumetric elements;

assigning tissue properties to the discretized volumetric elements based on the discretized volumetric elements' associated patient-specific 3D brain structure representations;

defining boundary conditions for estimating a temperature propagation vector based on laser ablation-related information obtained during a laser interstitial thermal therapy (LITT) procedure;

based on the defined boundary conditions and the assigned tissue properties, computing temperature propagation within the patient's brain during the LITT procedure;

based on the computed temperature propagation, estimating tissue damage within the patient's brain during the LITT procedure; and displaying a visual representation of the estimated tissue damage during the LITT procedure.

20. The system of claim 19, wherein the shape-constrained deformable brain model comprises a computerized 3D representation of a non-patient-specific human brain that preserves vertex-based correspondence during adaption to patient scans.

* * * * *